US00PP18552P3

(12) United States Plant Patent
Carruth

(10) Patent No.: US PP18,552 P3
(45) Date of Patent: Mar. 4, 2008

(54) SHRUB ROSE PLANT NAMED 'WEKCISBAKO'

(50) Latin Name: *Rosa hybrida*
Varietal Denomination: WEKcisbako

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 11/478,045

(22) Filed: Jun. 28, 2006

(65) Prior Publication Data

US 2008/0005815 P1 Jan. 3, 2008

(51) Int. Cl.
*A01H 5/00* (2006.01)

(52) U.S. Cl. ..... Plt./107

(58) Field of Classification Search ..... Plt./107
See application file for complete search history.

*Primary Examiner*—Kent Bell
*Assistant Examiner*—S. B. McCormick-Ewoldt
(74) *Attorney, Agent, or Firm*—Christie, Parker & Hale, LLP

(57) ABSTRACT

A new variety of shrub rose suitable for garden decoration, having flowers of flame red coloration.

1 Drawing Sheet

Classification: The present invention relates to a new *Rosa hybrida* plant.

Variety denomination: The new plant has a varietal denomination 'WEKcisbako'.

BACKGROUND OF THE INVENTION

This invention relates to a new and distinct variety of Shrub Rose. It has an undisseminated seedling as its seed parent with the following genetic origin (City of San Francisco×Baby Love) (not patented), and as its pollen parent the variety known as 'RADrazz' (U.S. Plant Pat. No. 11,836).

SUMMARY OF THE INVENTION

Among the features which distinguish the new variety from other presently available and commercial rose cultivars known to the inventor are the following combination of characteristics: its high degree of resistance to black spot and powdery mildew, its heavy suffusion of red pigmentation on the very tip of the sepal, its many stipitate glands on the surface of the bud and the peduncle, its several stipitate glands on the new shoots and its flame red coloration that last throughout the life of the flower. The plant has a bushy moderately spreading growing habit, suitable for outdoor garden decoration.

Asexual reproduction of the new variety by budding as performed in Kern County and Upland, Calif. shows that the foregoing and other distinguishing characteristics come true to form and are established and transmitted through succeeding asexual propagations. 'WEKcisbako' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, an undisseminated seedling by the following combination of characteristics: whereas 'WEKcisbako' bears medium sized flowers (about 6.3 to about 9.1 cm. in diameter) of flame red coloration, the undisseminated seedling bears significantly smaller flowers (about 4.2 to about 5.6 cm. in diameter) of medium pink coloration with a white center. The new variety is classified as a shrub rose with a bushy moderately spreading medium height growth habit, whereas the seed parent is classified as a miniature rose with a rounded and compact significantly shorter growing habit.

The new variety may be distinguished from its pollen parent, 'RADrazz' by the following combination of characteristics: whereas 'WEKcisbako' bears flowers of flame red coloration (between 46A and 53A on the upper surface of the newly opened flower) with single petalage (about 5 petals), 'RADrazz' bears flowers of significantly lighter red coloration (between 53C and 53D on the upper surface of the newly opened flower) with significantly heavier petalage (about 10 petals). The new variety has a high degree of resistance to powdery mildew, whereas the pollen parent is significantly less resistant to powdery mildew.

COMPARISON WITH THE CLOSEST COMMERCIALLY AVAILABLE CULTIVAR

The closest commercially available cultivar to the new variety is the pollen parent 'RADrazz'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of June. Phenotypic expression may vary with environmental, cultural and climatic conditions, as well as differences in conditions of light and soil.

FLOWER

The new variety sometimes bears its flowers singly, usually in clusters of two to six or more per stem. Flowers may be borne in somewhat regular rounded clusters on strong medium stems (about 19 to about 58 cm.). Outdoors, the plant blooms abundantly and nearly continuously during the growing season. The flowers have a slight tea fragrance.

BUD

The peduncle is about 1.2 to about 3.5 cm. in length, of average caliper (about 0.2 to about 0.3 cm. in diameter), and usually erect. It is rough with many stipitate glands. Peduncle color is between 144A and 146B sometimes lightly suffused, especially on the side exposed to the sun, with between 187B and 183B.

Before the calyx breaks, the bud is about 0.7 to about 1.1 cm. in diameter at the widest point, about 1.2 to about 1.7 cm. in length, and very pointed in shape. The surface of the bud bears some foliaceous appendages and many stipitate glands, usually with slender entire foliaceous parts extending beyond the tip of the bud about ¼ or more of its length. Bud color is between 146A and 146B sometimes lightly suffused, especially on the side exposed to the sun, with between 187B and 183B.

The sepals are about 2.0 to about 3.4 cm. in length and about 0.6 to about 0.8 cm. in width at the widest point. The outer surface color of the sepal is between 146A and 146B sometimes lightly suffused, especially on the side exposed to the sun, with between 187B and 183B. The very tip of the sepal is usually heavily suffused with between 187B and 183B. The inner surface color of the sepal is between 137B and 138B and covered with fine wooly tomentum; sepal margins are lined with some stipitate glands and hairs.

The receptacle of the flower is moderately short in length (about 0.4 to about 0.8 cm.) and somewhat thin in caliper (about 0.4 to about 0.7 cm. in diameter). The receptacle is moderately ovoid to somewhat rounded in form. Its surface is moderately smooth with some stipitate glands at the base and with thick fleshy walls. The receptacle color is between 146B and 137D.

As the petals open (after the calyx breaks), the bud is about 1.1 to about 1.4 cm. in diameter at the widest point, about 1.5 to about 2.6 cm. in length, and pointed to moderately ovoid in form. The color of the under surfaces of the newly opened petals is between 53A and 187B. At the point where the petal attaches, there is a small zone of between 8C and 10C. The color at the base of the upper surfaces of the newly opened petals is between 53A and 46A gradually suffusing toward the edge of the petals with between darker than 53A and 187B. At the point where the petal attaches, there is a small zone of between 2C and 4C.

BLOOM

When fully open, the bloom ranges from about 6.3 to about 9.1 cm. in diameter. Petalage is single with 5 petals and no petaloids. When partially open, the bloom form is cupped, and the petals are loosely cupped with petal edges moderately reflexed outward. When fully open, the bloom form is moderately cupped to somewhat flat, and the petals are more loosely cupped to slightly undulated with petal edges moderately reflexed outward.

PETALS

The substance of the petals is moderately heavy and of somewhat this thickness, with upper surfaces moderately satiny to somewhat velvety and under surfaces moderately shiny. The petals are about 3.0 to about 4.1 cm. in length and about 2.4 to about 3.9 cm. in width at the widest point. Petal margins are entire.

The petals are broadly obovate in shape with rounded apices and sometimes slightly notched with one notch.

Petaloids are absent from the flower.

NEWLY OPENED FLOWER

The under surface color of the petals is between 53C and 53B. At the point where the petal attaches, there is a moderately small zone of between 2C and 4C. On the upper surface of the petals, the color at the base of the petals is between 53C and 46B, gradually suffusing toward the edge of the petals with between 46A and 53A. At the point where the petal attaches, there is a moderately small zone of between 8C and 10C.

The general tonality of the newly opened flower is between 53C and 46B, gradually suffusing toward the edge of the petals with between 46A and 53A.

THREE-DAY-OLD FLOWER

The under surface color of the petals is between 53D and 53C. At the point where the petal attaches, there is a moderately small zone of between 155B and 155D. On the upper surface of the petals, the color at the base of the petals is between 53C and 46C, gradually suffusing toward the edge of the petals with between 53B and 53A. At the point where the petal attaches, there is a moderately small zone of between 155B and 155D.

The general tonality of the three-day-old flower is between 53C and 46C, gradually suffusing toward the edge of the petals with between 53B and 53A.

On the spent bloom, the petals usually drop off cleanly.

In June in Upland, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 95) and are arranged regularly about the pistils. The filaments are of medium length (about 0.4 to about 0.9 cm.) most with anthers. Filaments are between 6C and 7C at the base suffusing to near 22B in color. The anthers are somewhat small for the class and all open approximately at the same time. Anther color is between 22B and 187C when immature and between 163D and 200B at maturity. Pollen is moderately abundant and near 22C in color.

FEMALE REPRODUCTIVE ORGANS

Pistils vary in number (average about 25). The styles are even, moderately short in length (about 0.3 to about 0.6 cm.), average in caliper and moderately bunched. Stigma color is between 18B and 20C. Style color is near 4D usually heavily suffused with between 53B and 53C. Ovaries are all enclosed in the calyx.

Hips have not been observed on this variety when grown in Upland, Calif.

FOLIAGE

The compound leaves are usually comprised of three to five leaflets and are borne abundantly. The five-leaflet leaves are about 11.6 to about 14.1 cm. in length and about 9.5 to about 11.4 cm. in width at the widest point, moderately leathery to somewhat crisp in texture and glossy in finish. The terminal leaflets are about 4.8 to about 6.9 cm. in length and about 3.2 to about 4.9 cm. in width at the widest point, shaped obovate to somewhat oval with acuminate apices and rounded bases. Their margins are usually simply serrate.

The upper surface color of the mature leaf is between 147A and 139A. The under surface color of the mature leaf is between 147B and 139B. The upper surface color of the young leaf is between 146A and 146B, usually moderately suffused with between 187A and 183A. The under surface color of the young leaf is between 147B and 146B, usually heavily suffused with between 187B and 183A.

The rachis is average in caliper and rough. The upper side is shallowly grooved with some hairs and stipitate glands on the edges of the grooves. The under side of the rachis is rough with some stipitate glands and few small prickles. The rachis color is between 146B and 146D sometimes lightly suffused with between 187B and 183A.

The stipules are about 1.2 to about 1.9 cm. in length and of medium width (about 0.4 to about 0.6 cm.) with moderately long straight points that usually turn out at an angle of more than 45 degrees. The stipules color is between 137A and 146C sometimes lightly suffused with between 187B and 183A.

The petiole is average in caliper and rough. The upper side is shallowly grooved with some hairs and stipitate glands on the edges of the grooves. The under side of the petiole is rough with some stipitate glands and few small prickles. The petiole is about 1.4 to about 2.1 cm. in length and about 0.15 to about 0.2 cm in diameter at the widest point. The petiole color is between 146B and 146D sometimes lightly suffused with between 187B and 183A.

The plant displays a high degree of resistance to black spot and powdery mildew and an above average degree of resistance to downy mildew and an average degree of resistance to rust as compared to other commercial varieties grown under comparable conditions in Upland, Calif. The plant's winter hardiness and drought/heat tolerance are yet to be determined.

GROWTH

The plant has a bushy moderately spreading medium height growth habit (about 90 to about 112 cm. in height and about 56 to about 70 cm. spread at the widest point), with very full branching. It displays vigorous growth and the canes are of somewhat heavy caliper for the class.

The color of the major stems is between 146A and 147B. They bear many large prickles that are about 0.6 to about 0.8 cm. in length. The large prickles are angled moderately downward to slightly hooked with a medium length somewhat broad oval base; prickle color is between 164C and 166A. The major stem bears many small prickles of similar shape and coloration.

The color of the branches is between 146A and 146B. They bear many large prickles which are of similar size and shape to the large prickles on the major stems; prickle color is between 146D and 147C often moderately suffused with between 187B and 183A. The branches bear some small prickles of similar shape and coloration.

The color of the new shoots is between 146B and 146C often lightly suffused with between 187B and 183A. They bear many large prickles which are of similar size and shape to the large prickles on the major stems; prickle color is between 146D and 147C often moderately suffused with between 187C and 183C. The shoots bear several stipitate glands and several small prickles of similar shape and coloration to the large prickles.

I claim:

1. A new and distinct shrub rose plant of the variety substantially as described and illustrated herein.

* * * * *

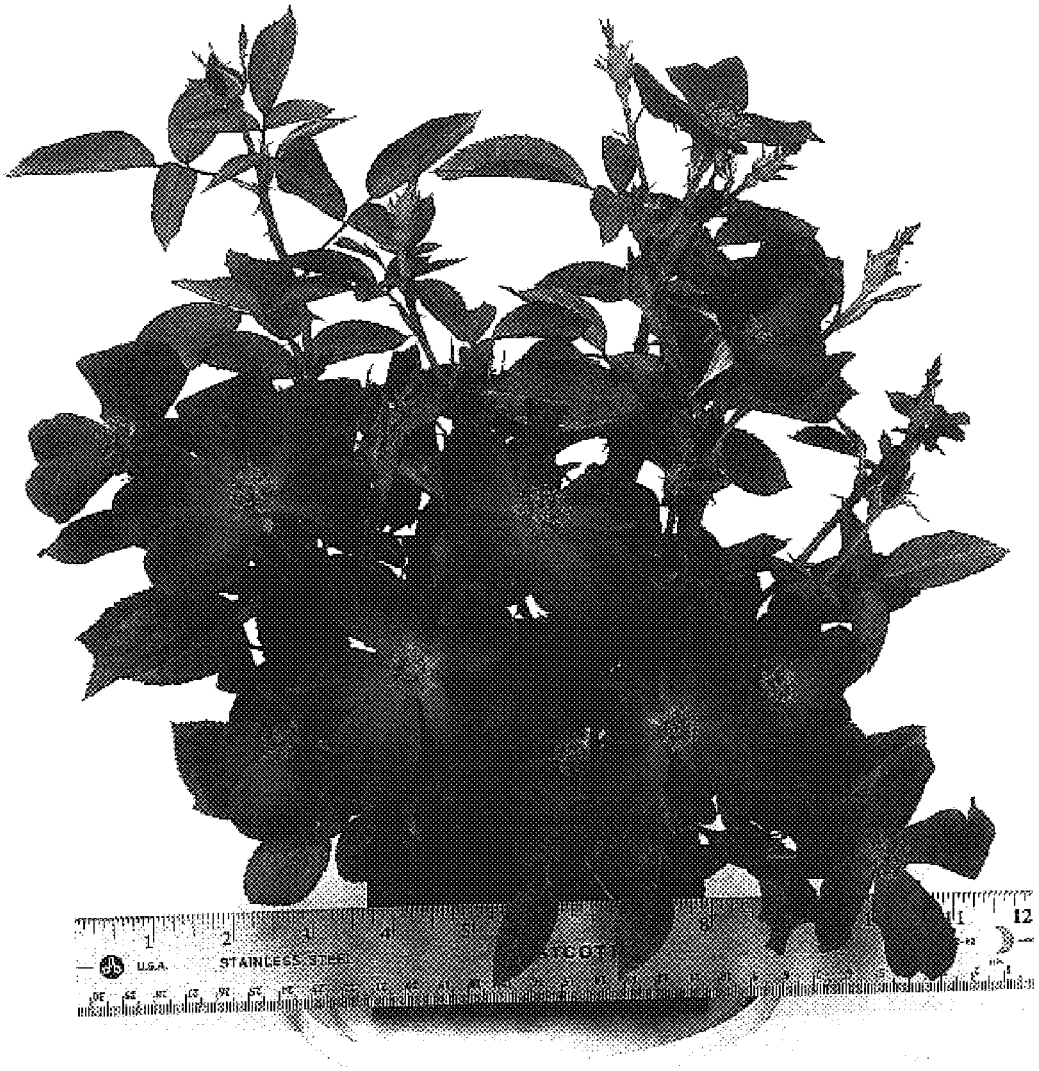
STAINLESS STEEL